United States Patent
Frimerman

(10) Patent No.: US 8,956,385 B2
(45) Date of Patent: Feb. 17, 2015

(54) INTEGRATED DISTAL EMBOLIZATION PROTECTION APPARATUS FOR ENDO-LUMINAL DEVICES SUCH AS BALLOON, STENT OR TAVI APPARATUS

(76) Inventor: Aharon Frimerman, Tel Aviv (IL)

( * ) Notice: Subject to any disclaimer, the term of this patent is extended or adjusted under 35 U.S.C. 154(b) by 210 days.

(21) Appl. No.: 13/332,431

(22) Filed: Dec. 21, 2011

(65) Prior Publication Data
US 2012/0330346 A1    Dec. 27, 2012

Related U.S. Application Data

(63) Continuation-in-part of application No. 12/758,850, filed on Apr. 13, 2010, now abandoned.

(60) Provisional application No. 61/425,262, filed on Dec. 21, 2010, provisional application No. 61/212,599, filed on Apr. 14, 2009.

(51) Int. Cl.
| | |
|---|---|
| *A61M 29/00* | (2006.01) |
| *A61F 2/01* | (2006.01) |
| *A61F 2/958* | (2013.01) |
| *A61B 17/3207* | (2006.01) |
| *A61F 2/04* | (2013.01) |
| *A61M 25/10* | (2013.01) |

(52) U.S. Cl.
CPC .......... *A61F 2/013* (2013.01); *A61F 2/958* (2013.01); *A61B 2017/320716* (2013.01); *A61F 2002/045* (2013.01); *A61M 25/104* (2013.01); *A61M 2025/1093* (2013.01); *A61F 2002/018* (2013.01); *A61F 2230/0006* (2013.01); *A61F 2230/008* (2013.01)

USPC .......................................................... 606/200

(58) Field of Classification Search
USPC .......................................................... 606/200
See application file for complete search history.

(56) References Cited

U.S. PATENT DOCUMENTS

| | | | | |
|---|---|---|---|---|
| 5,329,942 | A | * | 7/1994 | Gunther et al. ............... 128/898 |
| 2003/0055480 | A1 | | 3/2003 | Fischell et al. |

(Continued)

FOREIGN PATENT DOCUMENTS

WO    WO2010/119444    10/2010

OTHER PUBLICATIONS

"Cerebral embolism following transcatheter aortic valve implantation: comparison of transfemoral and transapical approaches". Webb JG et al. J Am Coll Cardiol. Jan. 4, 2011;57(1):18-28.

(Continued)

*Primary Examiner* — Darwin Erezo
*Assistant Examiner* — Michael Mendoza
(74) *Attorney, Agent, or Firm* — Edward Langer. Adv. and Patent Attorney

(57) ABSTRACT

An endoluminal catheterization device for providing protection against distal embolization of atherosclerotic debris and thrombi emboli resulting from an endoluminal catheterization procedure. The device is adapted to the new TAVI/PAVI methods to prevent the severe risk of brain embolization and stroke. The embolization protection device may also be an integral part of any other intra-luminal treatment or diagnostic device that may induce embolization, such as a balloon, stent, TAVI or atherectomy.

23 Claims, 21 Drawing Sheets

(56) References Cited

U.S. PATENT DOCUMENTS

| | | |
|---|---|---|
| 2003/0176886 A1 | 9/2003 | Wholey et al. |
| 2005/0228438 A1 | 10/2005 | Sachar et al. |
| 2006/0167491 A1 | 7/2006 | Wholey et al. |
| 2006/0265000 A1 | 11/2006 | Azizi |
| 2007/0106320 A1 | 5/2007 | Blix et al. |
| 2007/0135832 A1 | 6/2007 | Wholey et al. |
| 2007/0162071 A1 | 7/2007 | Burkett et al. |
| 2007/0244504 A1 | 10/2007 | Keegan et al. |
| 2007/0299466 A1 | 12/2007 | Sachar et al. |
| 2008/0300621 A1 | 12/2008 | Hopkins et al. |

OTHER PUBLICATIONS

"Embolic cerebral insults after transapical aortic valve implantation detected by magnetic resonance imaging." Ludwig J. et al. JACC Cardiovasc Interv. Nov. 2010;3(11):1126-32.

"Risk and fate of cerebral embolism after transfemoral aortic valve implantation: a prospective pilot study with diffusion-weighted magnetic resonance imaging." Thomas D et al. J Am Coll Cardiol. Apr. 6, 2010;55(14):1427-32. Epub Feb. 24, 2010.

* cited by examiner

INTEGRATED DISTAL EMBOLIZATION PROTECTION APPARATUS FOR ENDO-LUMINAL DEVICES SUCH AS BALLOON, STENT OR TAVI APPARATUS

CROSS REFERENCE TO RELATED APPLICATION

The present invention relates generally to the field of angioplasty, and more particularly to angioplasty devices providing protection against embolization. The present application is a Continuation-in-Part of U.S. patent application Ser. No. 12/758,850 filed Apr. 13, 2010 by the Applicant, now abandoned which is based on U.S. Provisional Application No. 61/212,599 filed Apr. 14, 2009, and the present Application is also based on U.S. Provisional Application No. 61/425,262 filed 21 Dec., 2010, the disclosure of which is hereby incorporated by reference.

BACKGROUND OF THE INVENTION

Coronary artery disease (CAD) affects almost 1.3 million Americans per year, making it the most common form of heart disease. CAD most often results from a condition known as atherosclerosis, which is the most common form of arteriosclerosis i.e. hardening of the arteries.

Atherosclerosis occurs when plaque forms inside the arteries. Plaque is made of cholesterol, fatty compounds, calcium and fibrin. As the plaque builds up, the artery narrows, making it more difficult for blood to flow through the arteries. When atherosclerosis occurs in a coronary artery, blood flow to the heart muscle is impeded. In time, the narrowed or blocked artery can lead to angina pectoris, Myocardial Infarct (MI) and possibly death. A similar processes can affect other arteries, such as the carotid, intra-cerebral, and renal arteries, as well as arteries of the upper and lower limbs, leading to stroke, renal failure, hypertension and malfunction of the limbs, depending on artery affected.

In order to reduce the risk of artery disease and its complications, one option is opening the artery narrowing induced by atherosclerosis, utilizing intra-lumen balloon inflation and/or intra-lumen stent deployment.

In balloon angioplasty, a guiding catheter is inserted through a small skin incision into an artery and advanced to the origin of the coronary artery. Next, a guide wire is advanced through the guiding catheter into the coronary artery and across the blockage site. Then, a long, thin catheter that has a small balloon on its tip (balloon catheter) is pushed over the guide wire. The balloon is inflated at the blockage site in the artery to flatten or compress the plaque against the artery wall, and is then deflated and withdrawn. Thus, the blockage is removed from at least a portion of the arterial lumen, and blood can flow more freely through the artery.

Another method for opening plaque blockage is stent deployment. A stent is a small mesh-like tube made of metal. The stent may be pre-crimped over a balloon on the tip of a balloon catheter and pushed over the guide wire (as explained above) to the blockage site, where it is then expanded and deployed by the pressure of the balloon inflation at the narrowed site, and as such, acts as a support or scaffold, keeping the vessel open. Stent procedures are usually used along with balloon angioplasty. The first balloon inflation prepares the narrowed site, and enables stent insertion and deployment by another balloon on which the stent is crimped on.

Alternatively, a self-expandable stent may be used, which does not require a balloon for deployment. Such stents are made of shape memory metal and are provided with a covering sheath that compresses the stent to a low profile prior to delivery to the deployment site. At the deployment site, the covering sheath is removed, and the shape memory metal enables the stent to regain its full diameter.

Such procedures may be used to open narrowing in arteries including coronary, carotid, intra-cranial, and renal arteries, and peripheral arteries in the legs and arms.

Unfortunately, these procedures pose a great risk to the patient as emboli, generated by the balloon inflation or stent deployment that crush the frail atherosclerotic plaque, or thrombotic material, may be released during them. Once released, these emboli have a high likelihood of getting lodged into the smaller vessels at a point of constriction downstream of their release point, causing the vessels to become occluded and preventing blood flow.

These adverse events may cause severe damage to the treated organ like myocardial infarction, stroke, renal failure or limb malfunction.

There are several known embolization protection devices based mainly on an additional small proximal or distal occluding balloon with some debris removal system, or a small filter attached to the guide wire with deployment and retrieval systems.

Examples of known embolization protection devices, include:

U.S. patent application Ser. Nos. 10/348,137, 11/387,366, 11/566,473 to Wholey et al;

U.S. patent application Ser. Nos. 11/763,118, 10/997,803 to Sachar et al;

U.S. patent application Ser. No. 11/271,653 to Blix et al;

U.S. patent application Ser. No. 09/952,375 to Fischell et al; and

U.S. patent application Ser. No. 09/845,162 to Wahr.

The above-mentioned devices have many limitations. The occluding balloon-based type induces ischemia since the occluding balloon stops the distal blood flow for a relatively long period. Moreover, the need for a special debris extraction catheter prolongs the procedure and increases its complexity.

The over-the-wire filter devices have a special guide wire with inferior crossing ability compared to the regular wires. The extra delivery sheath covers the filter prior to its deployment, increasing the wire profile, reducing its crossing ability and because of its larger size, may cause embolization. There is also difficulty delivering the filter to a proper site distally to the lesion and difficulty in maintaining its position during the procedure. The need for another retrieval system prolongs the whole procedure time.

It is no wonder that several clinical randomized studies showed that in a group of patients in which distal embolization protection devices were used, the overall adverse events were significantly higher than in the control group where such devices were not applied.

Therefore, there is a need for a new embolization protection device, which is an integral part of the intra-lumen device, which will decrease the risks of distal embolization during use of intra-lumen devices.

Trans Luminal Aortic Valve Implantation (TAVI) is a novel therapy which may be used as an alternative to standard surgical aortic valve replacement. The TAVI procedure is performed on the beating heart using catheterization methods without the need for a Sternotomy or a Cardiopulmonary Bypass. Currently, two devices are CE marked and the procedure may be performed via the transfemoral, or subclavian approaches in which the catheter carrying the valve is advanced retrogradlly into the aorta and the artificial valve is positioned at the native aortic valve annulus.

Another approach is the Transapical method which combines minimally invasive surgery and catheterization. The surgeon performs a small incision at the heart apex, through it, a catheter carrying the valve is advanced anterogradly and the artificial valve is positioned at the native aortic valve annulus. This Anterograde method is also called PAVI (Percutaneous Aortic Valve Implantation). This new field of interventional cardiology is growing rapidly and there are many companies developing new TAVI/PAVI devices. One major drawback of this new technique is multiple emboli dislodgment from the artificial valve deployment site which is usually heavily calcified. Brain MRI studies showed some degree of emboli into the brain in as many as about 70% of the TAVI cases.

SUMMARY OF THE INVENTION

Accordingly, it is a principal object of the present invention to overcome the limitations of prior art embolization protection devices by providing a distal embolization protection component as an integral part of an Endo-luminal catheterization device, and a simple deployment/retrieval method that does not change or interfere with the current Endo-luminal Transcatheter technique, while trapping any emboli that are released, and allowing blood to continue flowing without interference during the Endo-luminal catheterization procedure.

In accordance with a preferred embodiment of the present invention, there is provided an Endo-luminal catheterization device for providing protection against distal embolization of atherosclerotic debris and thrombi emboli resulting from an endoluminal catheterization procedure, said device comprising:

an endoluminal dilatation component mounted on a shaft, said shaft having at least one lumen; a flexible filter integrally mounted on said shaft; and a thin retraction filament extending through said at least one lumen in said shaft and emerging from an opening in said shaft, said retraction filament being attached to said flexible filter for controlling deployment and collapsing of said filter, wherein said flexible filter, when deployed, traps said atherosclerotic debris and thrombi emboli thus allowing blood flow to continue without interference during said endoluminal catheterization procedure.

In some embodiments, the dilatation component comprises a stent, such as a self-expandable stent. In some embodiments, the dilatation component comprises an angioplasty balloon, which may optionally have a stent crimped over it.

The purpose of the filter deployment ring is to open the proximal portion of the filter at the beginning of the endoluminal catheterization procedure, such that the filter is opened to the full size of the circumference of the artery at the treatment site. The artery is thus sealed, such that atherosclerotic debris and thrombi emboli released from the plaque during the procedure, are trapped inside the filter. The filter deployment ring is also used also for collapsing the filter at the end of the procedure, to a small profile, with the trapped emboli inside, for enabling retraction of the balloon catheter with the attached filter as one unit.

The present invention is designed for equipping any endo-luminal device known in the art including use of guidewires and standard balloon inflation-deflation methods such as a TAVI, balloon angioplasty device, stent, atherectomy, or any other intra-luminal treatment or diagnostic device that may induce embolization, with an integrated embolization protection component, positioned downstream to the treatment device. The integrated embolization protection component relinquishes the need for extra manipulation, hardware or overall procedure time.

The apparatus, including the treatment and protection components, is advanced to the lesion site, there the protection component is deployed before the balloon/stent/TAVI is deployed. Since these two elements are attached to the same catheter they are fixed together without axial movement, thus preventing movement-induced complications. The protection deployment and retrieval are very fast and easy to operate as will be shown in detail.

When the dilatation component, such as a balloon, and/or stent compresses and crushes the plaque impeding blood flow, pieces of the plaque are released into the bloodstream and can become lodged in smaller vessels downstream to the treatment site, and block them. To avoid such a scenario, a filter is connected to the dilatation component, downstream to it, and traps any emboli that are released, while allowing blood to continue flowing without interference.

According to a further embodiment of the present invention, the current distal embolization protection device is adapted to the new TAVI/PAVI methods to prevent the severe risk of brain embolization and stroke.

In accordance with some embodiments of the present invention, the filter deployment ring is connected to a thin retraction filament extending through a lumen in the shaft and emerging from an opening in the shaft, distal to the dilatation component, to avoid its entrapment by the dilatation component.

The retraction filament may optionally extend through a lumen which is also an inflation fluid lumen for a balloon. Alternatively, the retraction filament may extend through a dedicated lumen within the shaft.

In accordance with a second embodiment of the present invention, the retraction filament that is attached to the filter deployment ring, emerges from an opening in the shaft, proximal to an angioplasty balloon, and thereby the retraction filament runs over the entire length of the balloon. The device for a blood vessel angioplasty balloon, according to this embodiment, cannot have a stent pre-crimped over it because the retraction filament and filter can get tangled with a stent, if it were there, at the stage of the device withdrawal.

According to some embodiments of the present invention, the filter deployment ring is tightened by pulling the retraction filament connected to the filter deployment ring. The tightened filter deployment ring causes the filter to close, containing in it trapped atherosclerotic debris and thrombi emboli.

According to an alternative embodiment of the present invention, the filter is composed entirely of a memory metal such as Nitinol, and as such, may be deployed and closed without using the filter deployment ring.

According to some embodiments, the device of the present invention further comprises a separate retraction filament tube proximal to the dilatation device, and joining the hollow shaft, wherein the retraction filament extends through the shaft, and a locking device enabling and disabling forward and backward movement of the retraction filament, wherein the locking device locks the retraction filament onto the retraction filament tube through which the retraction filament passes.

According to some embodiments, wherein the dilatation device comprises a balloon, the device further comprises a balloon inflation/deflation device configured as a syringe having a plunger proximal to the shaft, and connected to the shaft via an inflation tube, wherein the balloon inflation/deflation device injects inflation fluid through the inflation tube into the balloon for inflation, and withdrawing fluid from the balloon for deflation.

Optionally, the balloon is reversibly and repeatedly inflatable.

According to some embodiments, the filter deployment ring is deployed by unlocking the locking device and thereby releasing the thin retraction filament connected to the filter deployment ring, such that the ring returns to its original shape by memory.

According to some embodiments, the device of the present invention further comprises a safety stopper for ensuring that deployment of the filter occurs before balloon inflation, wherein the safety stopper is attached to the retraction filament and is situated at the connection point of the inflation tube with the shaft, thus blocking the entrance of inflation fluid for inflating the balloon, when the retraction filament is pulled and the filter is not yet deployed.

According to some embodiments, the safety stopper is pushed forward with the forward movement of the retraction filament when deploying the filter, and the stopper is then removed from the connection point of the inflation tube to said shaft so that said inflation fluid is allowed to flow through the shaft and inflate the balloon.

According to some embodiments, the shaft is wider in diameter beyond the connection point of the inflation tube to the shaft, for the purpose of accommodating the safety stopper.

According to some embodiments, the device further comprises a bulbous area formed in the shaft situated distally to the wider section of the shaft, wherein said bulbous area is large enough to contain the safety stopper once the filter is deployed and allow fluid to flow through it, and wherein distally to the bulbous area the shaft continues at a regular width.

The safety stopper optionally comprises at least one of silicon and rubber.

According to some embodiments, the length of the wider section of the shaft together with the length of the bulbous area is equal to the distance the retraction filament is pushed forward when the filter is deployed.

In some embodiments, the balloon is partially surrounded by the filter so that when the balloon is inflated it will further deploy the filter by pushing against it.

In some embodiments, the device further comprises a stent that is pre-crimped over the balloon, and deployment of the stent is achieved by inflation of the balloon.

In some embodiments, the diameter of the shaft is approximately two millimeters.

In some embodiments, the diameter of the balloon before inflation is 0.5 to 0.7 millimeters for coronary balloons, and the diameter of the balloon when inflated is approximately 2 to 4 millimeters, and the diameter of the balloon after deflation is approximately 2.5 millimeters.

In some embodiments, the diameter of the balloon for coronary stents is 1.1 to 1.5 millimeters.

In some embodiments, the filter deployment ring comprises a shape memory metal and the flexible filter is made of one of a shape memory metal and a very thin polymeric material.

In some embodiments, a diameter of the flexible filter before deployment is 0.5 to 1 millimeter in diameter, and the maximal size of said filter at the ring site when it is deployed is 2.5 to 5 millimeters in diameter.

According to some embodiments, the filter deployment ring comprises a shape memory metal, such as Nitinol.

According to a further embodiment of the present invention, the current distal embolization protection device is adapted to the new TAVI/PAVI methods to prevent the severe risk of brain embolization and stroke. The embolization protection device may also be an integral part of any other intraluminal treatment or diagnostic device that may induce embolization, such as a balloon, stent, TAVI or atherectomy. Similar to the coronary protection device the TAVI protection device is an integrated part of the catheter carrying the valve and is attached to the catheter downstream to the artificial valve. Since the TAVI/PAVI protection filter is attached to the catheter downstream to the artificial valve, it can be used for any artificial valve deployment apparatus and method such as a balloon, a self expandable mechanism or any other mechanisms that open the artificial valve at the native valve annulus and fixate it in place.

In accordance with the preferred embodiments of the present invention there is provided a method for performing an endoluminal catheterization procedure and providing protection against distal embolization resulting in said endoluminal catheterization procedure, said method comprising:

inserting an endoluminal catheterization device, comprising an endoluminal dilatation component mounted on a shaft, said shaft having a flexible filter mounted integrally thereon and a thin retraction filament extending through said shaft and emerging from an opening in said shaft, said retraction filament being attached to said flexible filter for controlling its deployment and collapse by releasing and pulling said retraction filament; and expanding said dilatation component, wherein said deployed flexible filter, traps atherosclerotic debris and thrombi emboli that are released from said crushed plaque said expansion of said dilatation component, thus allowing blood flow to continue without interference during said endoluminal catheterization procedure.

The method for distal embolization protection during an endoluminal catheterization procedure comprises first inserting the device at the treatment site, then deploying the flexible filter by releasing the retraction filament, and then expanding the dilatation component, such as by deploying a self expanding stent, or inflating an angioplasty balloon, which may deploy a stent or a valve-carrying stent, which crushes the plaque. The dilatation balloon is then deflated or the self expanding stent is fully deployed, and by so doing, emboli are released from the plaque and are captured by the deployed filter, while allowing blood to flow freely through it. The procedure ends by pulling the retraction filament which collapses the filter to a small profile with the emboli trapped in it, enabling withdrawal of the device out of the artery.

A feature of the present invention is a safety stopper, which is optionally substantially conical in shape, and is responsible for assuring that the balloon inflation will occur only once the filter is deployed, and not prior to deployment. The stopper does not allow inflation of the balloon if the filter is not deployed yet. This feature eliminates the possibility of human error, since an error in the order of the deployment of the balloon and filter would cause emboli to be released from the plaque into the blood stream without a filter to trap it.

Additional features and advantages will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF THE PREFERRED EMBODIMENTS

It is a principal object of the present invention to provide health care to an atherosclerosis patient by providing an endoluminal catheterization device comprising an endoluminal dilatation component, such as a balloon, with or without a stent, or a self-expanding stent, or a balloon with a valve-carrying stent, and a flexible filter as an integral part of the angioplasty device. The filter allows blood to flow through it but can also capture and remove from the blood vessel matter such as thrombi or atherosclerotic debris, thus preventing distal embolization.

Figure 1:
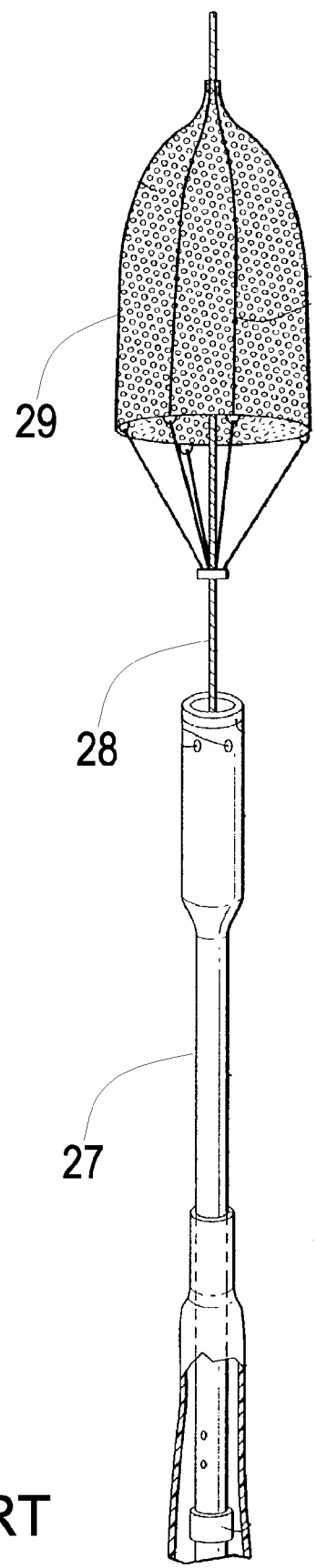
FIG. 1 is a prior art embolization protection device.

Referring now to FIG. 1, there is shown a prior art illustration of an embolization protection device. A filter assembly 29 is disposed on a guide wire 28, distal to a shaft 27. The filter 29 is not mounted directly on shaft 27, therefore deployment is more difficult, as explained in the background. This is in contrast to the inventive solution as disclosed in the description of the present invention herein below.

Figure 2A:
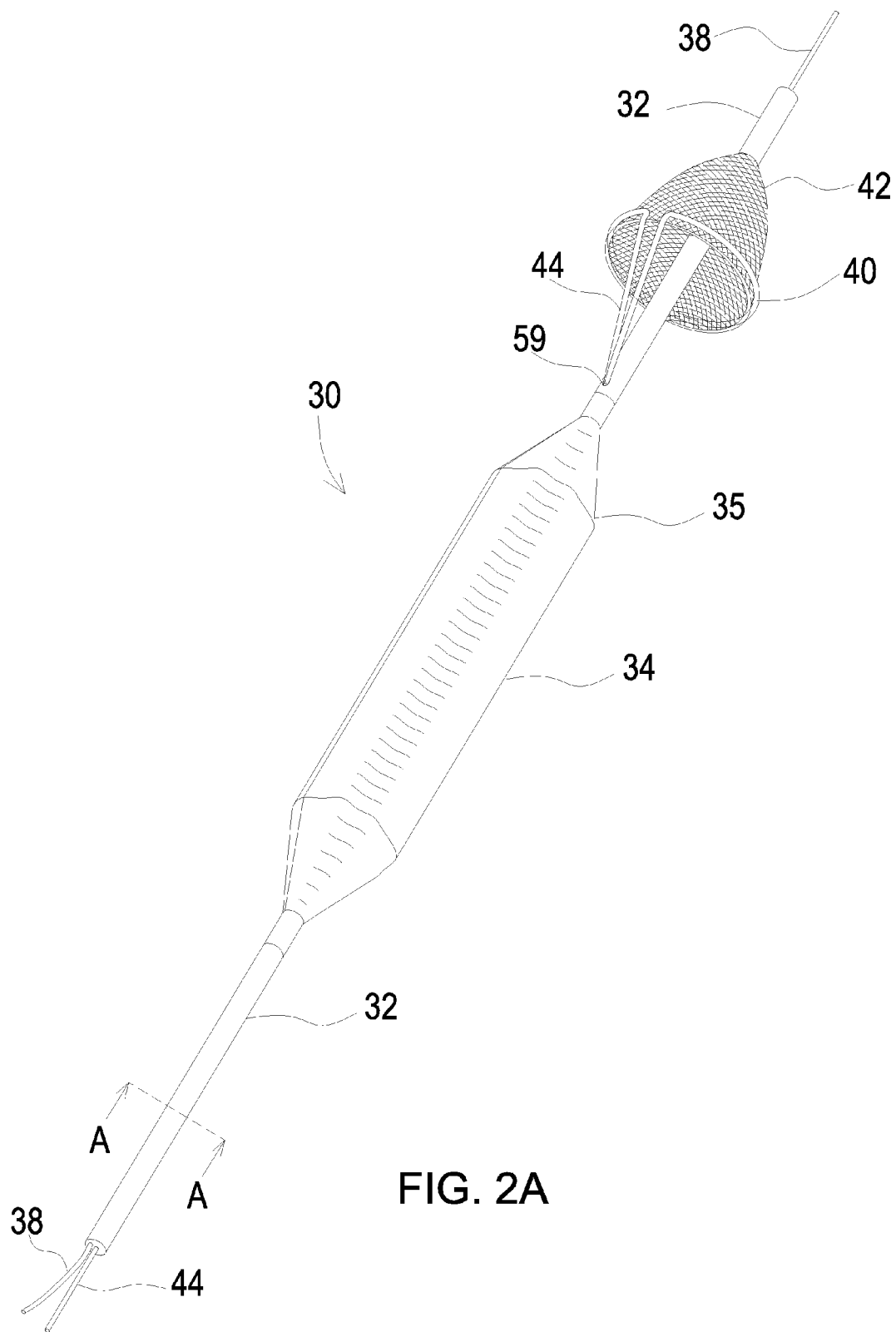
FIG. 2A shows a perspective view of a dilatation balloon with a distal embolization device.

Referring now to FIG. 2A, there is shown a perspective view of a device 30 for balloon angioplasty with an embolization protection component according to a preferred embodiment of the present invention. The inventive device 30 comprises a shaft 32, dilatation balloon 34, retraction filament 44, flexible filter 42 and filter deployment ring 40. In FIG. 2A, device 30 is depicted mounted on a guide wire 38.

Filter 42 may optionally comprise either a shape memory metal, comprising an alloy such as copper-zinc-aluminium-nickel, copper-aluminium-nickel, or nickel-titanium, (for example, Nitinol), or a mesh of very thin polymeric material (for example, ultra high molecular weight polyethylene). The pores of the filter should be of sufficient size to allow free passage of blood cells, while trapping atherosclerotic debris and thrombi emboli. Preferably, the pores are in the range of 30 to 50 microns.

As seen in FIG. 2A, dilatation balloon 34 is mounted on shaft 32, which extends beyond the distal end 35 of balloon 34. The diameter of shaft 32 is selected to enable deployment of shaft 32 within an artery. For example, the diameter of a shaft for deployment within a coronary artery is approximately 1 millimeter, or less.

As known in the art of balloon angioplasty, shaft 32 includes a guide wire lumen 39 (shown in FIGS. 2B and 2C) from a proximal end of shaft 32 passing through the distal tip of shaft 32, allowing balloon 34 to be guided along a deployed guidewire to a location in the vasculature. Additionally, as known in the art of balloon angioplasty, shaft 32 also includes an inflation fluid lumen 43 (see FIGS. 2B and 2C) providing fluid communication with the inner volume of balloon 34, allowing inflation and deflation of balloon 34 by introduction or removal of inflation fluid from the inner volume of balloon 34.

Device 30 further comprises a retraction filament 44 allowing an operator to collapse and/or release filter deployment ring 40. Retraction filament 44 passes from the proximal end to the distal end of shaft 32 through a lumen in shaft 32, which is separate from guide wire lumen 39, and emerges from an opening 59 in shaft 32 to attach to filter deployment ring 40.

Figure 2B:
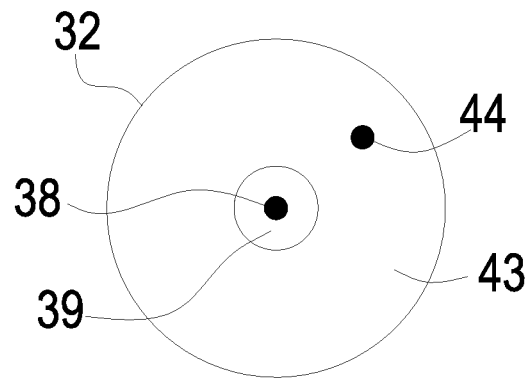
FIG. 2B shows a cross-section along section lines A-A of an embodiment of the device of FIG. 2A.

As shown in FIG. 2B, the lumen in shaft 32 through which retraction filament 44 passes may optionally comprise inflation fluid lumen 43, which is preferably coaxial with guide wire lumen 39, such that shaft 32 comprises at least two lumens.

Figure 2C:
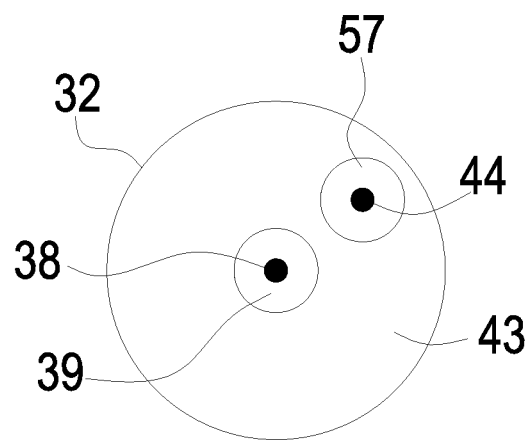
FIG. 2C shows a cross-section along section lines A-A of an alternative embodiment of the device of FIG. 2A.

Alternatively, as shown in FIG. 2C, retraction filament 44 may pass through a dedicated lumen 57 in shaft 32, isolated from inflation fluid lumen 43, such that shaft 32 comprises at least three lumens.

Filter deployment ring 40, which controls deployment and collapsing of filter 42, is disposed around the proximal opening of filter 42, and comprises a shape memory metal such as Nitinol or the like. When retraction filament 44 is pulled so as to tighten filter deployment ring 40, filter 42 is retained in a collapsed form.

When retraction filament 44 is released, filter deployment ring 40 returns to its original size and shape, thereby releasing pressure on filter 42, which is allowed to return to its original conical shape.

Figure 3A:
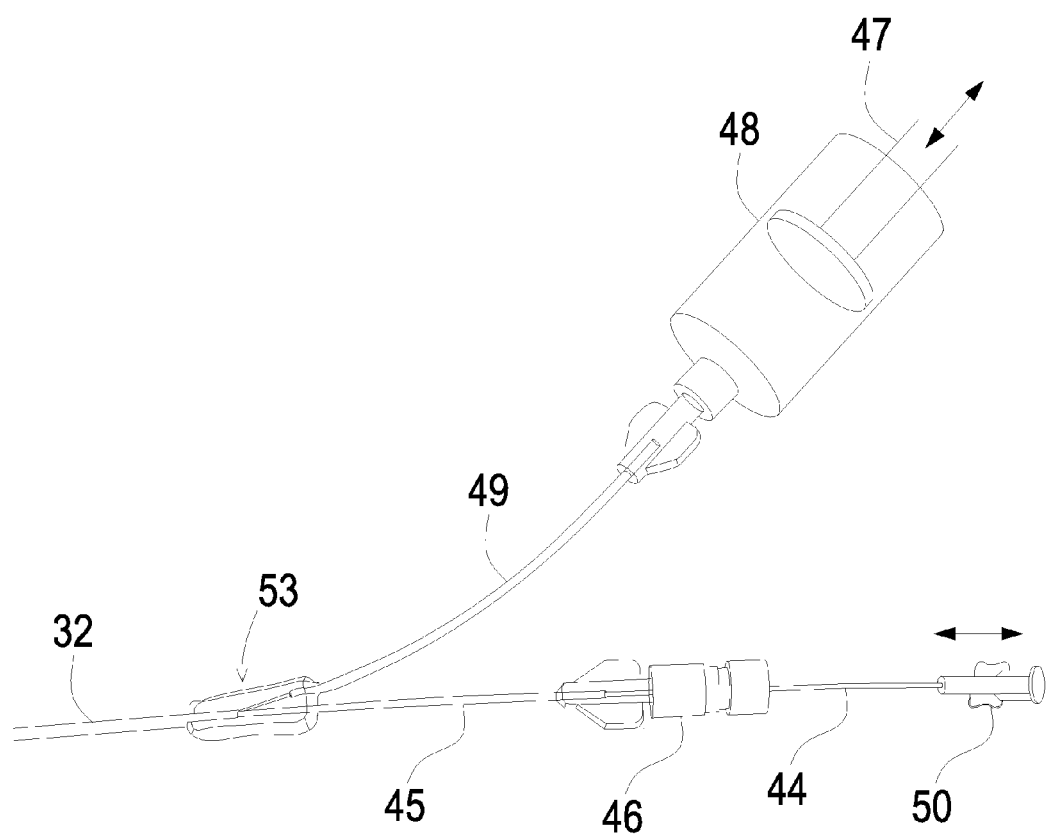
FIG. 3A shows a balloon inflation/deflation device, a retraction filament and a retraction filament locking device.

Referring now to FIG. 3A, there is shown the proximal part of the embolization device 30. The retraction filament 44 has a handle 50 on its proximal side, for moving the retraction filament 44 back and forth. The retraction filament 44 enters a filament tube 45 at the point where an external locking device 46 is situated. Locking device 46 can be twisted to the right or to the left, to lock and unlock the retraction filament 44 onto filament tube 45, so that the ability to move the retraction filament 44 back and forth is controlled. Retraction filament 44 covered by filament tube 45 enters shaft 32. Filament tube 45 may optionally be continuous with retraction filament lumen 57 of FIG. 2A or 2B.

As part of the device 30 there is provided a balloon inflation/deflation device 48 configured as a syringe having a plunger 47. The balloon inflation/deflation device 48 is attached to an inflation tube 49 entering shaft 32 at connection point 53. The inflation device is provided for the purpose of inflating balloon 34 by pushing fluid through tube 49 into balloon 34 via the hollow portion of shaft 32, and for deflating balloon 34 by withdrawing the fluid from balloon 34.

Figure 3B:
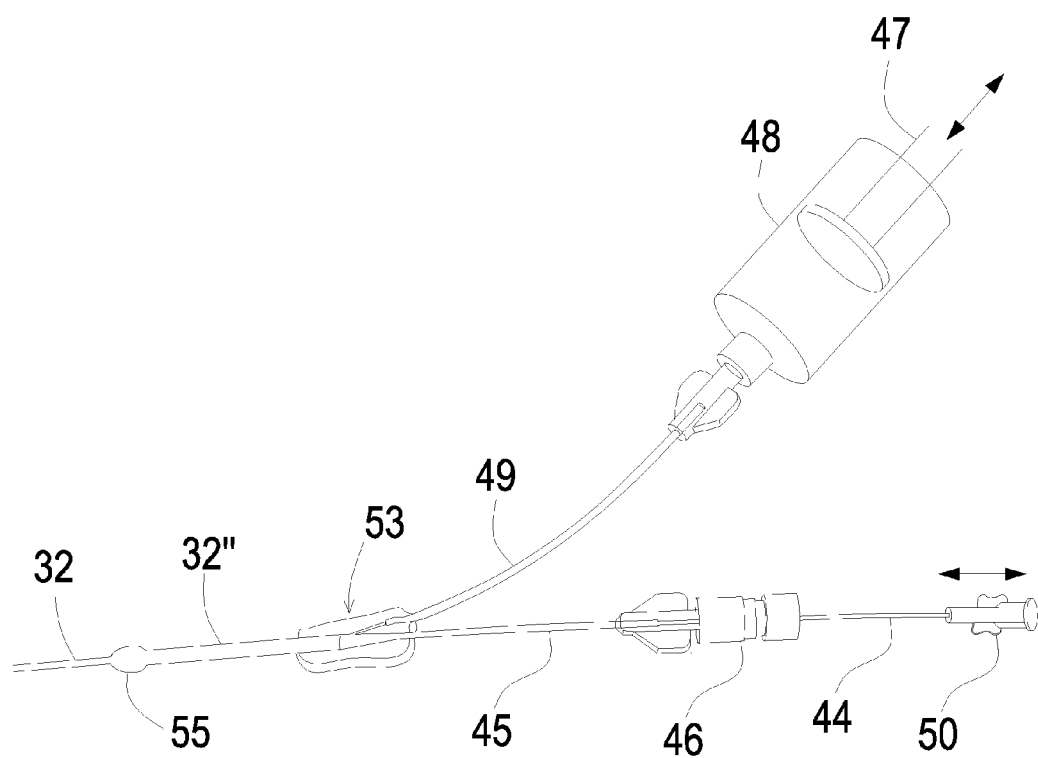
FIG. 3B shows the device of FIG. 3A with a bulbous modification on a shaft for accommodating a safety stopper.
Figure 3C:
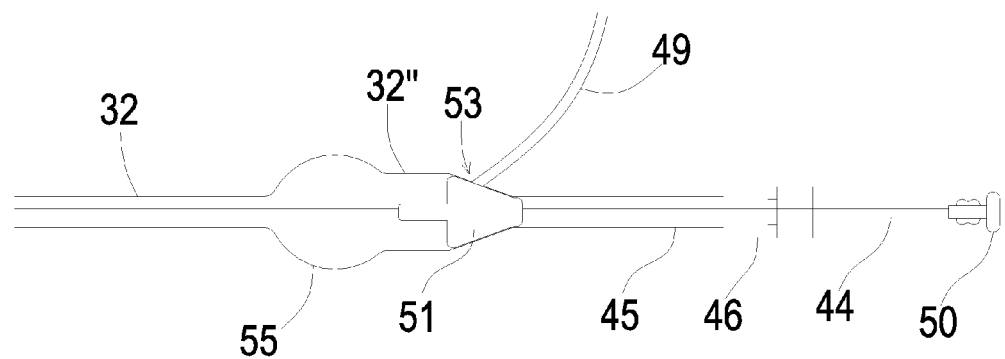
FIG. 3C shows a safety stopper blocking balloon inflation.
Figure 3D:
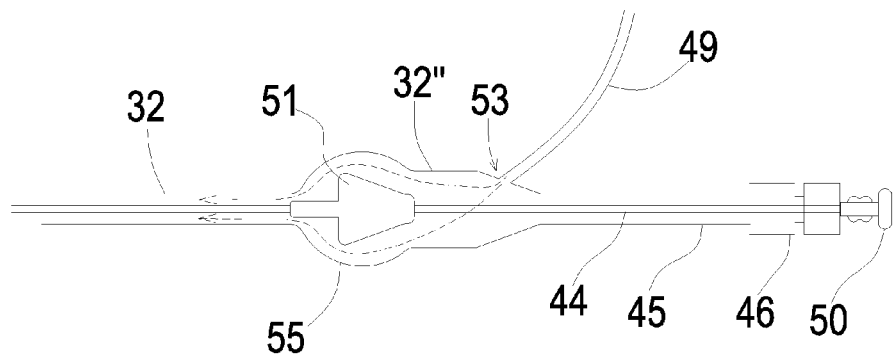
FIG. 3D shows the safety stopper allowing balloon inflation.

Referring now to FIGS. 3B-3C-3D, there is shown the device 30 as shown in FIG. 3A, modified to accommodate a feature of the invention which is the provision of a safety stopper 51, which is optionally substantially conical-shaped. The stopper 51 is responsible for ensuring that inflation of the balloon 34 will occur only once filter 42 is deployed, and not prior to deployment.

To accommodate stopper 51, section 32" of shaft 32 is provided with a width slightly greater than that of shaft 32, beyond connection point 53. A portion of section 32" is shaped to form a bulbous area 55, and distal to area 55 shaft 32 narrows and continues with the same width of the shaft 32 of FIG. 3A.

The following description discloses the mode of operation of safety stopper 51.

When retraction filament 44 is pulled, safety stopper 51, made of rubber, silicon or the like, is situated at connection point 53, thus blocking the entrance of the inflation fluid into section 32" so that it is not possible to inflate balloon 34. At this point, filter 42 is closed, since retraction filament 44 is pulled. Once locking device 46 is unlocked and then retraction filament 44 is released and moved forward, it moves the stopper 51 along with it, since they are connected to each other. The stopper 51 moves into section 32", thereby clearing the connection point 53 and allowing fluid to pass therethrough.

As stated, section 32" is slightly wider beyond connection point 53, in order for the stopper 51 to fit therein. At the connection point 53, stopper 51 fits the internal circumference of section 32" of shaft 32, so it blocks any fluid from entering it. After the wider section 32" of shaft 32, there is a bulbous shaped area 55.

When filter 42 is being deployed, stopper 51 is pushed into area 55 with the forward movement of filament 44. Bulbous shaped area 55 is large enough to contain stopper 51 and also allow fluid to flow around the stopper 51, so that when stopper 51 is pushed to bulbous area 55, shaft 32 is not blocked and balloon 34 inflation is allowed. Distal to bulbous area 55, the shaft 32 is narrower than section 32". The length of section 32" plus bulbous area 55 is equal to the length that retraction filament 44 is pushed forward to fully deploy filter 42.

FIGS. 4-9 illustrate the use of device 30 in an angioplasty procedure.

Figure 4:
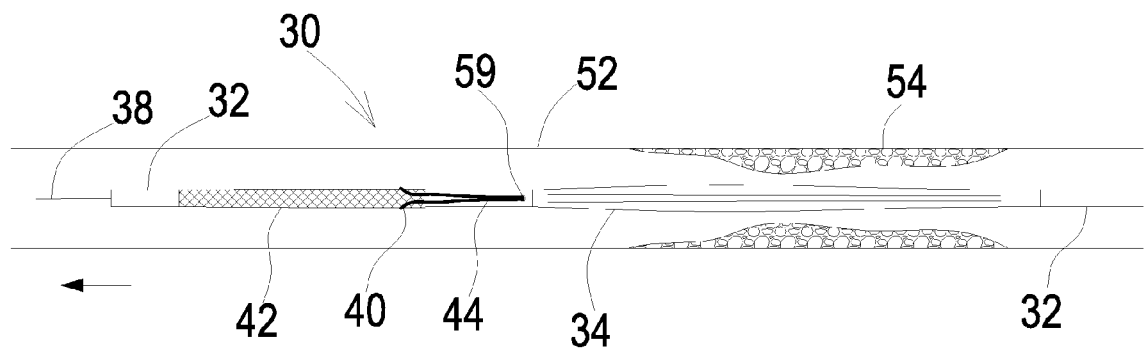
FIG. 4 shows a dilatation balloon with an embolization protection device lodged in a restricted blood vessel.

Referring now to FIG. 4, there is shown the device 30 at the initial stage of an angioplasty procedure, with non-inflated balloon 34 lodged in a blood vessel 52, with the balloon 34 positioned where the atherosclerotic plaque 54 is obstructing blood vessel 52. Filter 42 is collapsed and retained by retraction filament 44.

The size in diameter of the non-inflated balloon 34 is 0.5-0.7 millimeters for coronary balloons and 1.1-1.5 millimeters for coronary stents. For intra-cerebral arteries the size of the device is similar. For larger arteries like carotid or peripheral arteries, the size may increase 2-3 fold.

Figure 5:
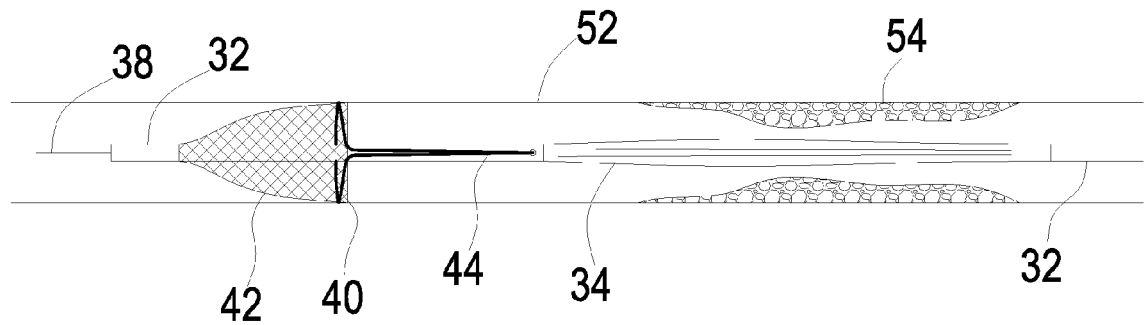
FIG. 5 shows the balloon of FIG. 4 with the embolization protection device deployed.

Referring now to FIG. 5, there is shown the device 30 during an angioplasty procedure, when filter 42 has been deployed by unlocking the locking device 46 and releasing the retraction filament 44 through shaft 32. Once the filament 44 is released, the filter deployment ring 40 surrounding filter 42, is no longer tightly drawn by the retraction filament 44, and ring 40 is free to return by memory to its original shape, allowing filter 42 to deploy so as to fit the internal circumference of the blood vessel 52. Thus filter 42 is released from its collapsed form.

The size of filter 42 before deployment is 0.5-1 millimeter in diameter. The maximal size of the filter at the ring site when it is deployed is 2.5-5 millimeter in diameter for coronary arteries.

Figure 6:
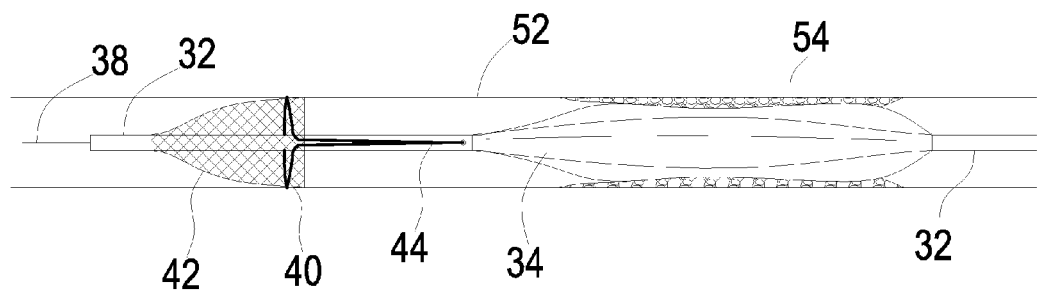
FIG. 6 shows the balloon of FIG. 4 inflated.

Referring now to FIG. 6, there is shown the device 30 with balloon 34 inflated and therefore pressing against plaque 54 on the walls of blood vessel 52. The pressure against the plaque 54 causes it to break up into small pieces which when they migrate with the blood flow are called emboli 56 (see FIG. 7). The size of the inflated balloon 34 is approximately 2-5 mm in diameter.

The sizes of both balloon 34 and filter 42 are 2-5 times larger when the angioplasty procedure is to be done in other arteries like carotid, renal or the peripheral arteries.

Figure 7:
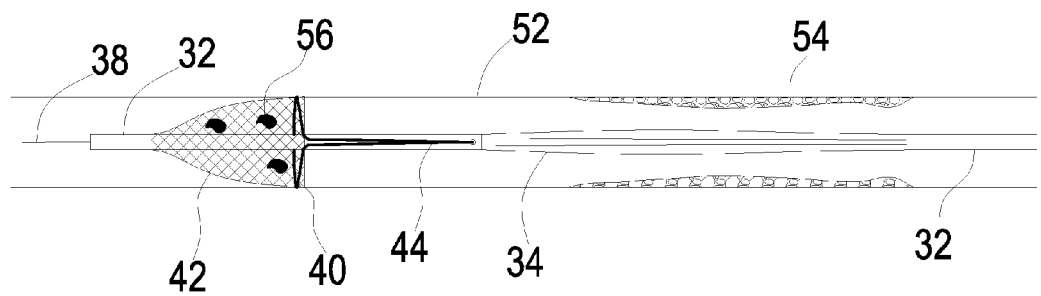
FIG. 7 shows the balloon of FIG. 4 deflated and emboli are captured in the protection device.

Referring now to FIG. 7, there is shown the device 30 with deflated balloon 34, and the layer of atherosclerotic plaque 54 is reduced because it was crushed and compressed by balloon 34, while inflated. The still deployed filter 42 traps any emboli 56 that are released from plaque 54, while allowing blood to continue flowing without interference through the porous filter. These emboli 56, if allowed to remain in blood vessel 52, can block smaller vessels downstream to blood vessel 52, and may cause, for example, infarction or stroke (depending on the treated artery) that may ultimately result in death.

In accordance with the principles of the present invention, the risk of small vessel downstream blockage by released emboli from the crushed plaque is eliminated since the filter deployment ring 40 seals the artery distally to the treatment site and the emboli flow into the porous filter wherein they are trapped. The present invention thus provides a device that traps the emboli and allows the blood to flow freely during the angioplasty procedure, thus eliminating the risk of downstream blockage and preserving flow during the procedure.

The balloon 34 inflation-deflation cycle can be repeated as many times as necessary while the filter is still deployed.

The size of the deflated balloon 34 (after initial inflation) is approximately 1-1.5 mm in diameter for coronary arteries, 2-5 times larger for other arteries.

Figure 8:
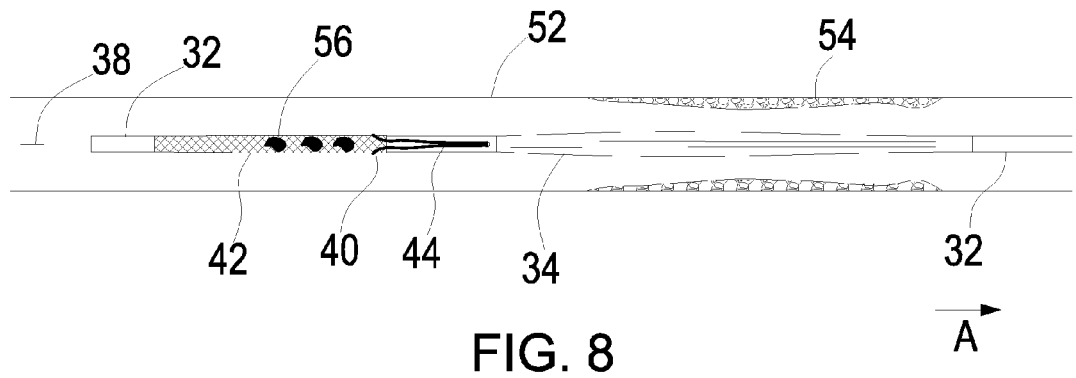
FIG. 8 shows the balloon of FIG. 4 with the protection device closed and containing released emboli, retracting from the artery.

Referring now to FIG. 8, there is shown device 30 after completion of the angioplasty procedure. The balloon 34 has been deflated and filter 42 is collapsed, containing in it trapped emboli 56. The filter 42 is closed by pulling retraction filament 44, and therefore tightening the filter deployment ring 40, surrounding filter 42, causing filter 42 to collapse to a small profile of 1-1.5 mm in diameter.

The device 30 is shown being retracted from vessel 52 (arrow A).

Figure 9:
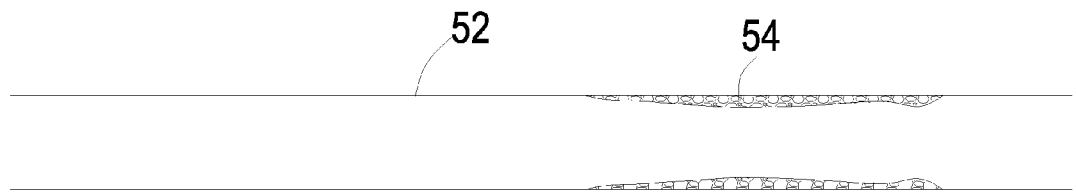
FIG. 9 shows the unrestricted blood vessel after treatment.

Referring now to FIG. 9, there is shown blood vessel 52, after removal of the device 30. As a result of the treatment, the layer of atherosclerotic plaque 54 is reduced and therefore vessel 52 is less obstructed and blood can flow more freely through the vessel.

FIGS. 10-15 illustrate another preferred embodiment of the device 30 for use in an angioplasty procedure with the addition of a stent.

Figure 10:
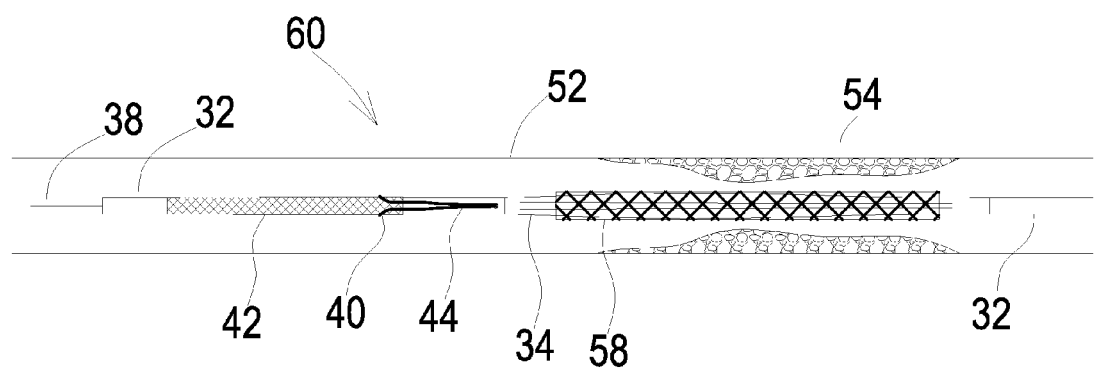
FIG. 10 shows a dilation balloon and stent with a distal embolization device lodged in a restricted blood vessel.

Referring now to FIG. 10, there is shown an alternative embodiment of the present invention, featuring a dilatation balloon and stent 58 with an embolization protection device 60. As shown, the device 60 is not yet deployed and is lodged in blood vessel 52 at the initial stage of the procedure.

Figure 11:
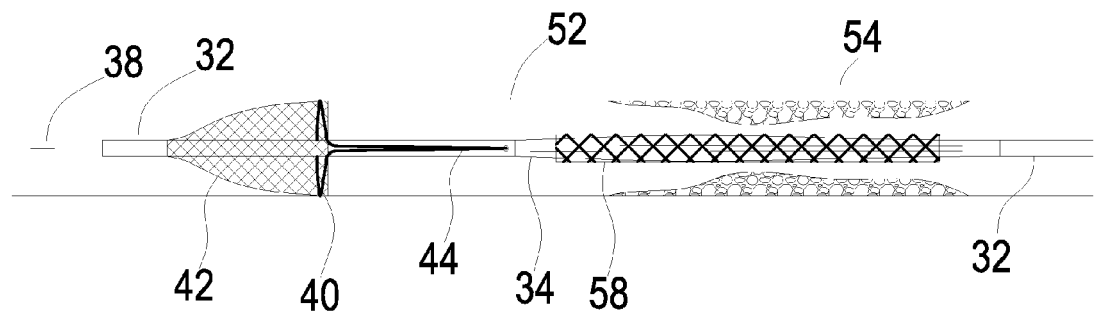
FIG. 11 shows the balloon and stent of FIG. 10 with the embolization protection device deployed.

Referring now to FIG. 11, there is shown the device 60 of FIG. 10, with filter 42 deployed, by releasing filter deployment ring 40 by the release of retraction filament 44.

Figure 12:
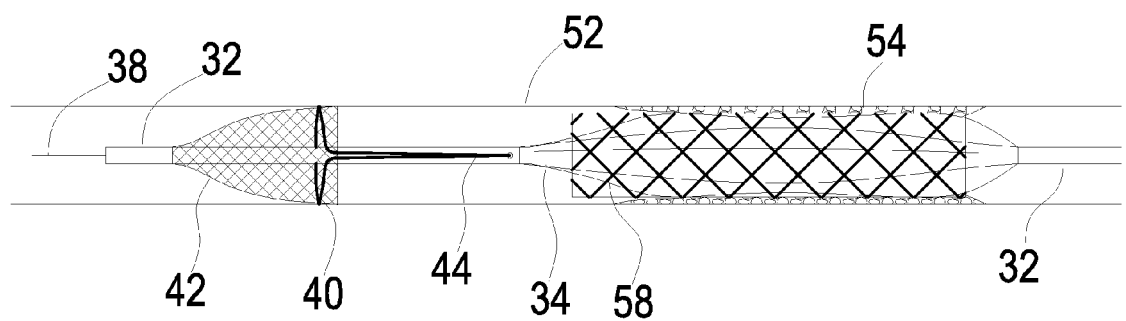
FIG. 12 shows the balloon and stent of FIG. 10 inflated and deployed, respectively.

Referring now to FIG. 12, there is shown the device 60 with balloon 34 inflated, causing stent 58 mounted on balloon 34 to deploy and to expand to fit the circumference of constricted vessel 52 and crush against plaque 54 on the walls of blood vessel 52, and thereby open the plaque narrowing the artery. During this process the plaque 54 is broken into small pieces called emboli 56.

Figure 13:
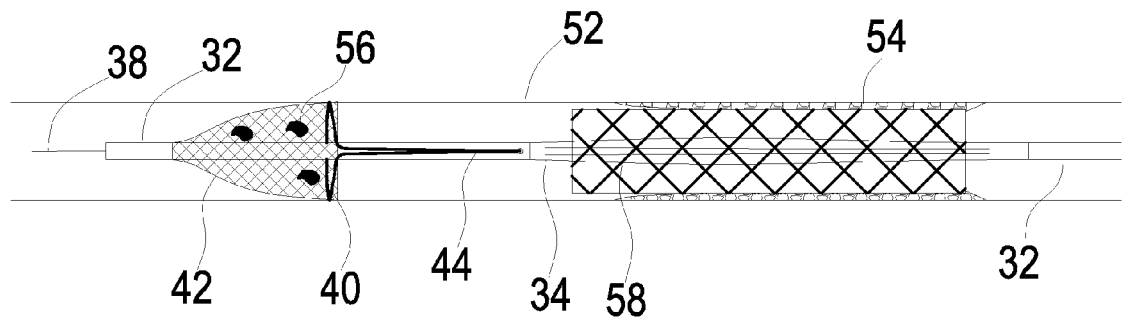
FIG. 13 shows the balloon and stent of FIG. 10 deflated and emboli are captured in the protection device.

Referring now to FIG. 13, there is shown the device 60, with balloon 34 deflated, thus releasing emboli 56 from plaque 54 flowing downstream to balloon 34 and getting trapped by deployed filter 42. The porous filter 42 allows blood to flow through it and therefore does not block the blood flow.

Figure 14:
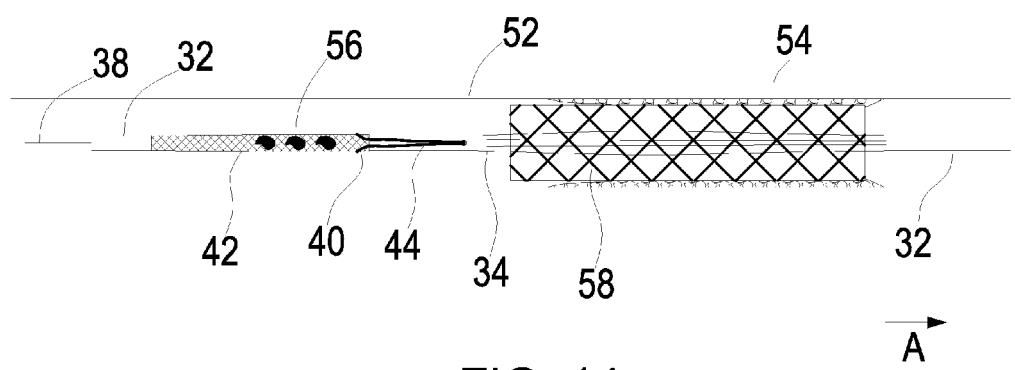
FIG. 14 shows the balloon and stent of FIG. 10 with the protection device closed and containing released emboli, retracting from the artery.

Referring now to FIG. 14, there is shown the device 60 with filter 42 closed, containing trapped emboli 56 in it. The filter 42 is closed by pulling retraction filament 44 which in turn pulls filter deployment ring 40 which is disposed around proximal opening of filter 42. The filter 42 collapses into a small profile, as in the first embodiment (FIG. 8). In this embodiment, the small profile of the closed filter 42 is essential so as to avoid getting entangled with stent 58 when it is withdrawn from vessel 52, through deployed stent 58.

The device 60 is retracted from blood vessel 52, as indicated by arrow A.

Figure 15:
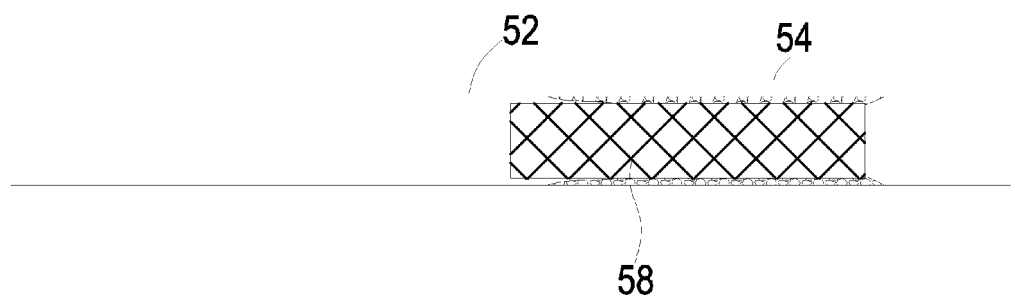
FIG. 15 shows the unrestricted blood vessel, with stent, after treatment.

Referring now to FIG. 15, there is shown the stent 58 deployed at the plaque 54 site, after treatment, thus keeping the treatment site open.

Figure 16:
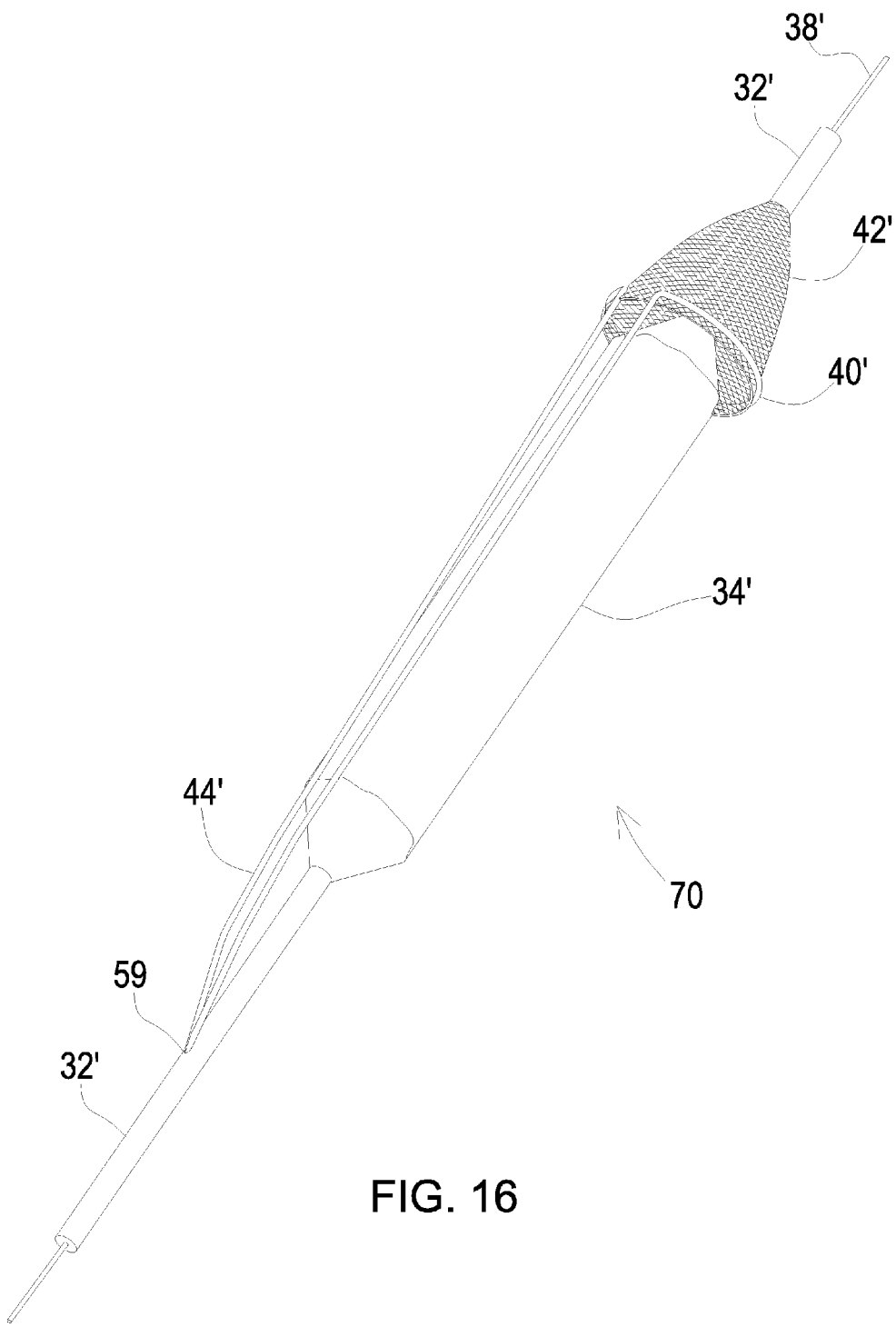
FIG. 16 shows a perspective view of a dilatation balloon with a distal embolization device, which cannot be used with a stent.

Referring now to FIG. 16, there is shown a perspective view of a device 70 for balloon angioplasty according to a preferred embodiment of the present invention. The device is meant only for a balloon without a stent, in an alternative to the embodiment of FIG. 2.

The retraction filament 44' is released from an opening 59 in shaft 32' proximal to balloon 34', and is attached to a thin metal memory filament and continues all the way to filter 42' which is distal to balloon 34', where it forms a ring and surrounds it as described in FIG. 2. Filter 42' surrounds a portion of the distal end of balloon 34', so that when balloon 34' is inflated it further deploys filter 42' by pushing against it.

Figure 17:
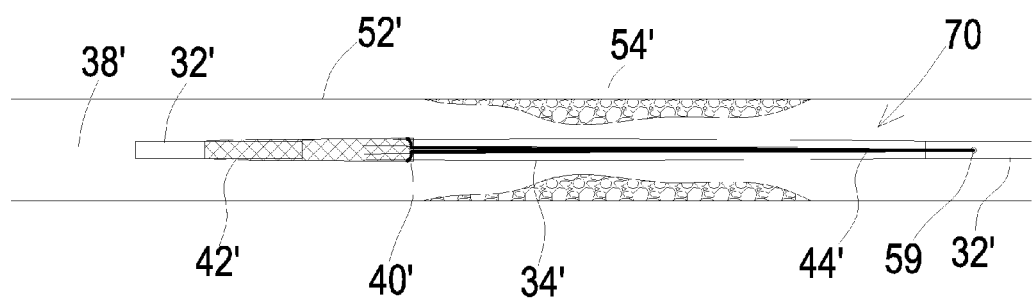
FIG. 17 shows the dilatation balloon of FIG. 16, lodged in a constricted blood vessel.

Referring now to FIG. 17, there is shown device 70 lodged in blood vessel 52', in the initial stage of the angioplasty procedure, as described in FIG. 4.

Figure 18:
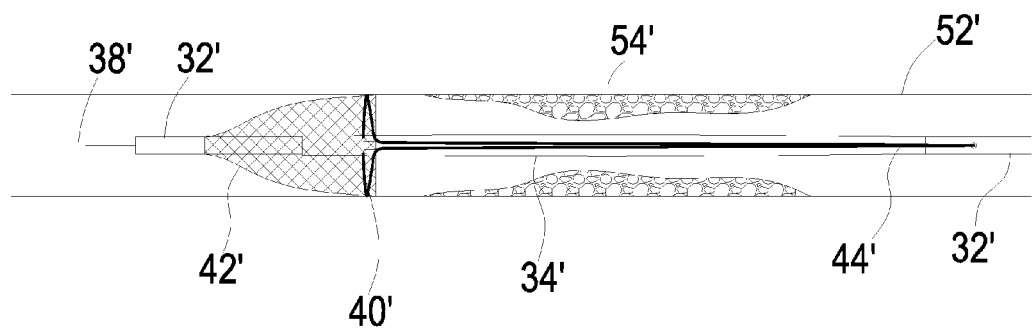
FIG. 18 shows the dilatation balloon of FIG. 16, with the embolization protection device deployed.

Referring now to FIG. 18, there is shown device 70 with filter 42' deployed, prior to balloon 34' inflation.

Figure 19:
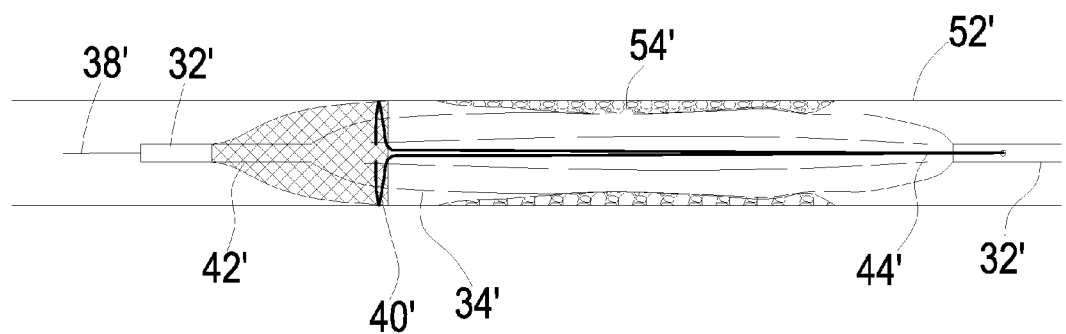
FIG. 19 shows the dilatation balloon of FIG. 16, with the balloon inflated.

Referring now to FIG. 19, there is shown device 70 with balloon 34' inflated. Since the balloon 34' is partially surrounded by the filter 42', the balloon 34' comes into contact with filter 42' as it is inflated, and this inflation further deploys filter 42'.

Figure 20:
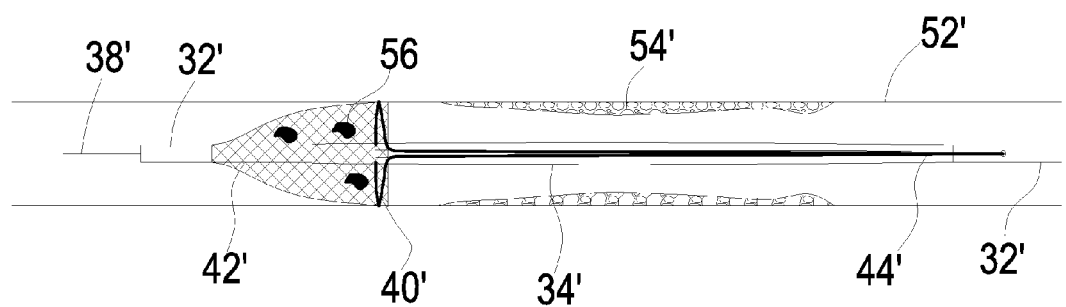
FIG. 20 shows the dilatation balloon of FIG. 16, with the balloon deflated and emboli are captured in the embolization protection device.

Referring now to FIG. 20, there is shown balloon 34' deflated, thereby releasing emboli particles 56 from the crushed plaque 54' which are trapped in still-deployed filter 42', with filter 42' allowing blood to flow through it so as not to obstruct the blood flow.

Figure 21:
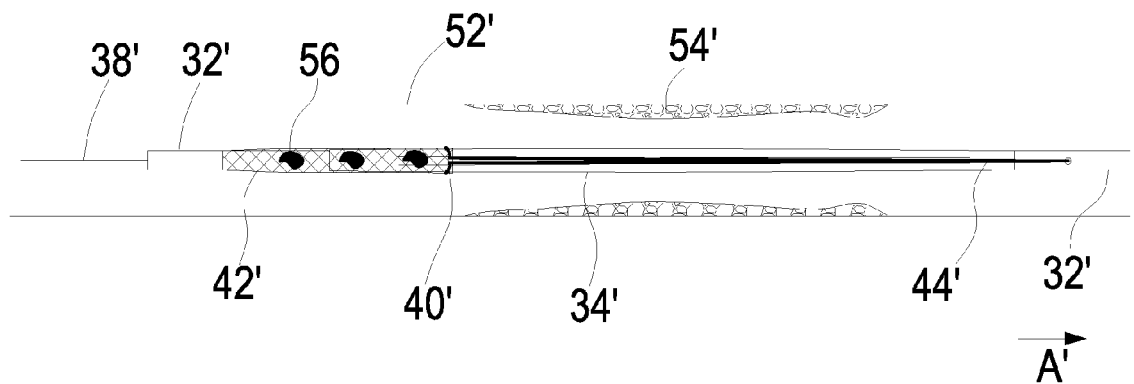
FIG. 21 shows the dilatation balloon of FIG. 16, with the embolization protection device closed.

Referring now to FIG. 21, there is shown filter 42' collapsed, with emboli 56 trapped within, being withdrawn from vessel 52' (arrow A).

Figure 22:
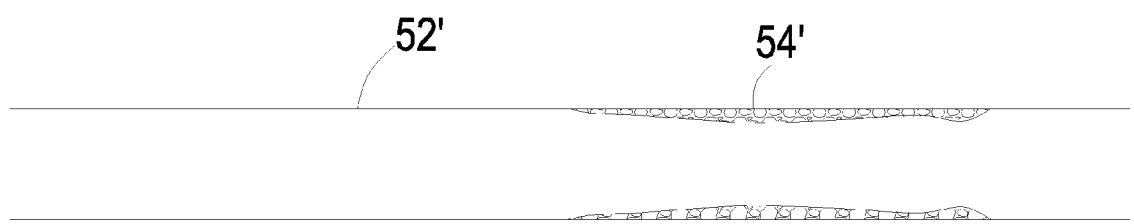
FIG. 22 shows the blood vessel after treatment.

Referring now to FIG. 22, there is shown blood vessel 52' having dilated plaque 54' after successful balloon angioplasty treatment.

Referring now to FIGS. 23 to 26 there is shown an alternative embodiment 80 of the device of the present invention, wherein the dilatation component comprises a self expandable stent 72.

Figure 23:
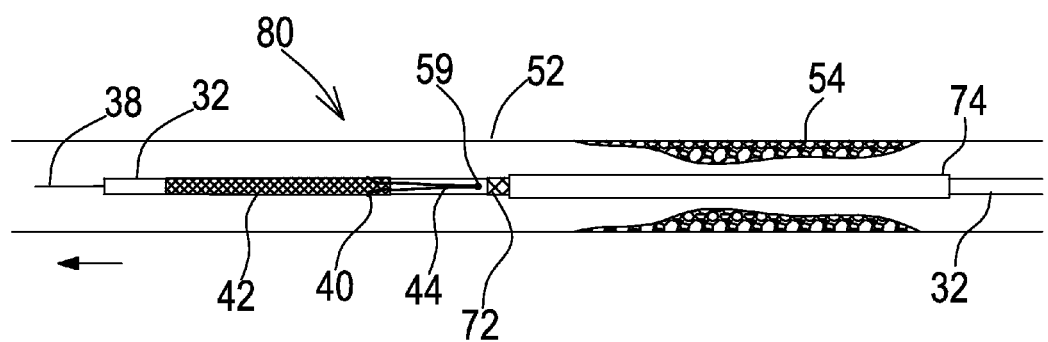
FIG. 23 shows an alternative embodiment of the device of the present invention, comprising a self expanding stent in a collapsed configuration, with the embolization protection device closed, prior to deployment.

Referring now to FIG. 23 there is shown device 80 prior to deployment, wherein stent 72 and filter 42 are in the collapsed configuration within vessel 52, adjacent to plaque 54. Device 80 is provided with protective sheath 74 which retains stent 72 in a collapsed configuration, having a narrow profile, and which is gradually pulled back from stent 72 during deployment, enabling expansion of stent 72.

Figure 24:
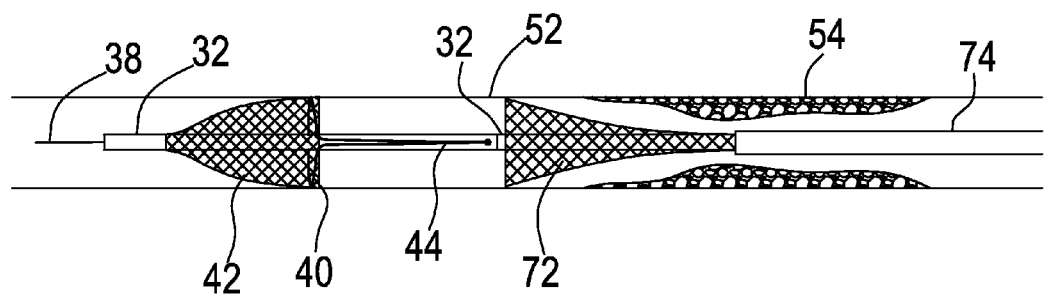
FIG. 24 shows the device of FIG. 23 during deployment, wherein the embolization protection device is open.

Referring now to FIG. 24 there is shown device 80 partially deployed, wherein upon removal of protective sheath 74 from a portion of stent 72, by gently pulling towards proximal end of stent 72, the portion of stent 72 which is released from sheath 74 expands to its full diameter, thereby pressing against plaque 54. Filter 42 is opened prior to full deployment of stent 72 to enable trapping of any emboli released from plaque 54 during deployment of stent 72.

Figure 25:
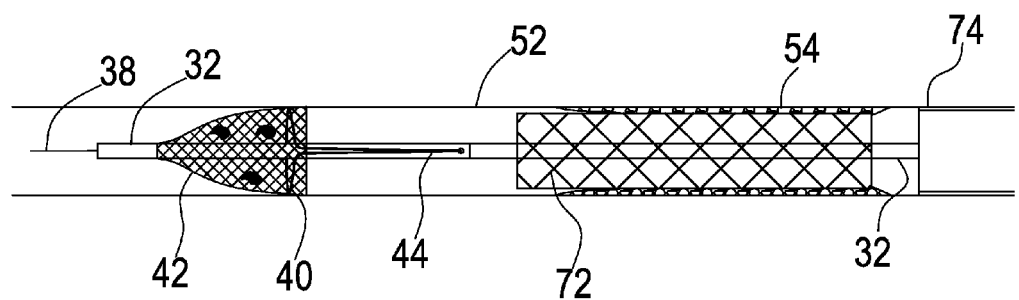
FIG. 25 shows the device of FIG. 23 fully deployed.

Referring now to FIG. 25 there is shown a device 80 wherein protective sheath 74 is totally removed beyond distal end of stent 72, such that stent 72 is fully deployed, crushing plaque 54. Emboli 56 released from plaque 54 are trapped within filter 42.

Figure 26:
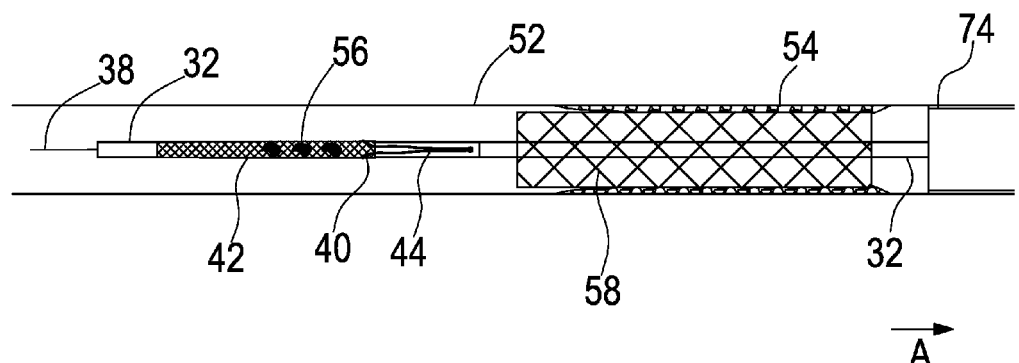
FIG. 26 shows the device of FIG. 23 following deployment, with emboli captured within the embolization protection device.

As shown in FIG. 26, following deployment of stent 72 and release of emboli 56 from crushed plaque 54, filter 42 is collapsed, such that emboli 56 are trapped within filter 42 prior to removal of device 80 from blood vessel 52.

Figure 27:
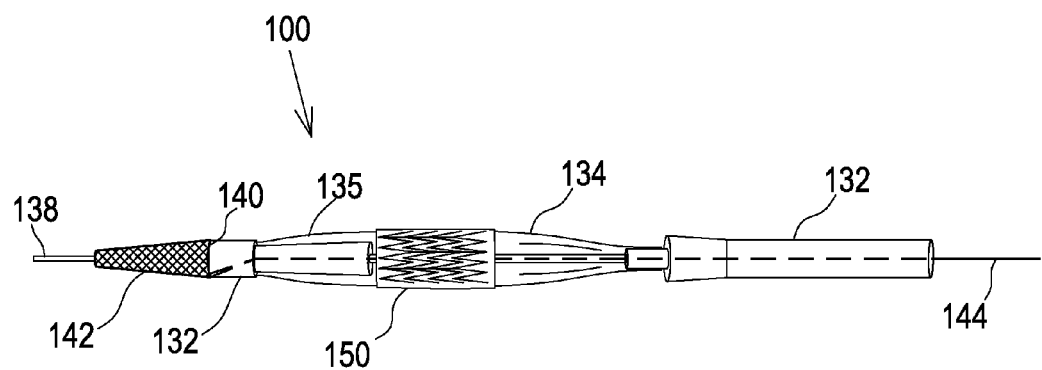
FIG. 27 shows a perspective view of the Percutaneous Trans Apical (PAVI) approach with the distal embolization device in the closed configuration.
Figure 28:
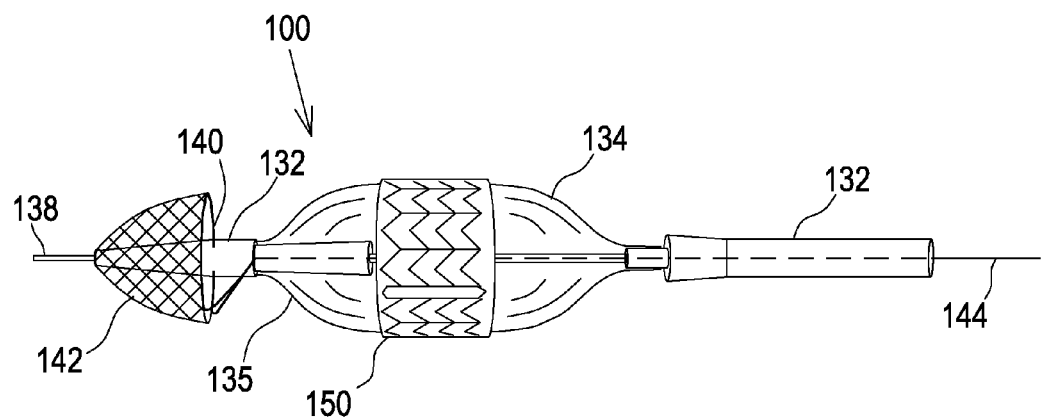
FIG. 28 shows the PAVI of FIG. 27 with the distal embolization device in the open configuration.

Referring now to FIGS. 27-28 there is shown the embolization protection device 100 according to the Trans Apical approach to valve implantation, according to a preferred embodiment of the present invention. The inventive device 100 comprises a guide wire 138, dilatation balloon 134, retraction filament 144, flexible filter 142, device delivery catheter shaft 132 and an aortic valve carrying stent 150.

The valve carrying stent 150 is not limited to only an aortic valve, but may also be a pulmonic or tri-cuspid valve-carrying stent.

Filter 142 may optionally comprise either a shape memory metal, comprising an alloy such as copper-zinc-aluminum-nickel, copper-aluminum-nickel, or nickel-titanium, (for example, Nitinol), or a mesh of very thin polymeric material (for example, ultra high molecular weight polyethylene). The pores of the filter should be of sufficient size to allow free passage of blood cells, while trapping atherosclerotic debris and thrombi emboli. Preferably, the pores are in the range of 30 to 50 microns.

Filter deployment ring 140, which controls deployment and collapsing of filter 142, is disposed around the proximal opening of filter 142, and comprises a shape memory metal such as Nitinol or the like. When retraction filament 144 is pulled so as to tighten filter deployment ring 140, filter 142 is retained in a collapsed form.

When retraction filament 144 is released, filter deployment ring 140 returns to its original size and shape, thereby releasing pressure on filter 142, which is allowed to return to its original conical shape.

When the filter 142 is made entirely of Nitinol or any other memory-metal, the opening and closing of the filter 142 may be controlled without deployment ring 140. However, when filter 142 is made of very thin polymeric material, then the ring 140 should be present for the opening and closing of filter 142.

Dilatation balloon 134 is mounted on catheter shaft 132, which extends beyond distal end 135 of balloon 134. The diameter of shaft 132 is selected to enable deployment of shaft 132 within an artery and a left ventricle apex. For example, the diameter of a shaft for deployment within a coronary artery is approximately 1 millimeter, or less.

The device 100 works in a similar way to device 30 as described in FIGS. 2A-8. In the case of device 100, first a small incision is performed at the heart apex. Through this puncture catheter shaft 132 carrying the valve 150 is advanced anterogradlly. Retraction filament 144 is then released by the operator to release filter deployment ring 140 thus deploying filter 142. Once filter 142 is deployed it is safe to inflate balloon 134, which is positioned at the native aortic valve annulus, so as to deploy the valve-carrying stent 150, mounted on the middle of balloon 134. Once valve 150 is deployed balloon 134 is deflated (not shown), thus releasing emboli fragments downstream from the valve deployment site, which become trapped in filter 142. Filter 142 is then collapsed by pulling retraction filament 144, and device 100 is ready to be withdrawn from the heart, leaving the valve carrying stent 150 at the valve deployment site.

The size of the PAVI device 100 and TAVI device 100' prior to deployment is approximately 5-8 mm, and after deployment is approximately 25-35 mm about 5-8 times larger than the Angioplasty devices 30 and 70.

Figure 29:
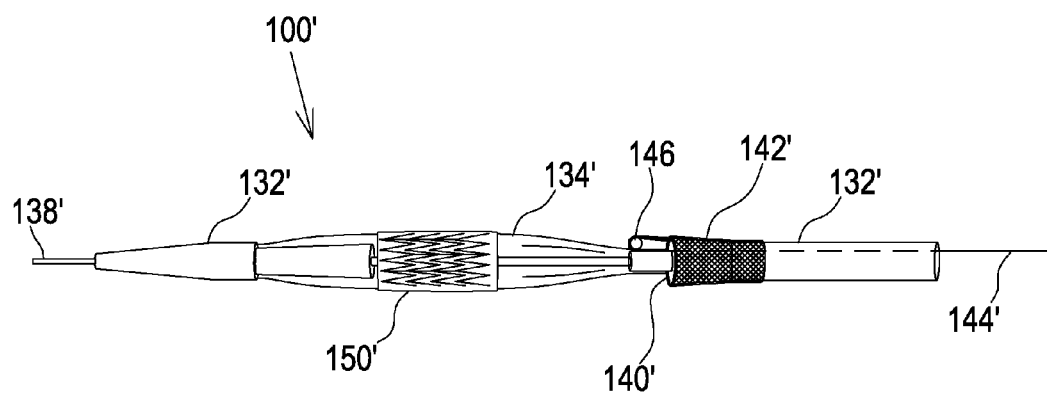
FIG. 29 shows a perspective view of the Trans-Femoral (TAVI) approach, with the distal embolization device in the closed configuration.

Referring now to FIG. 29 there is shown the embolization protection device 100' according to the Trans Femoral approach (TAVI) to a valve implantation, according to a preferred embodiment of the present invention. Device 100' is similar to device 100 except for the filter 142' being positioned before the valve-carrying stent 150', unlike device 100 where the filter 142 is positioned after the valve-carrying stent 150.

In the Trans Femoral (TAVI) approach, catheter shaft 132' carrying aortic valve 150 is advanced retrogradlly into the aorta, and artificial valve 150' is positioned at the native aortic valve annulus. Because the blood flows from valve 150' towards filter 142', filter 142' must be downstream to valve 150'. This way, filter 142' is opened in the direction opposite that of filter 142 of device 100. In order to control the opening and closing of filter 142' by the operator, retraction filament 144' exits catheter shaft 132' proximal to balloon 134' and distal to filter 142', and there it is diverted 180® towards the opposite direction, towards filter 142', by a stationary or pivotable point designated as retraction filament reversing-point 146, and filament 144' is wrapped around filter 142', forming filter deployment ring 140'. This design allows the operator to control the deployment of filter 142' by pulling filament 144', and to close filter 142' by releasing filament 144'.

The valve carrying stent 150' is not limited to only an aortic valve, but may also be a pulmonic or tri-cuspid valve-carrying stent.

Figure 30:
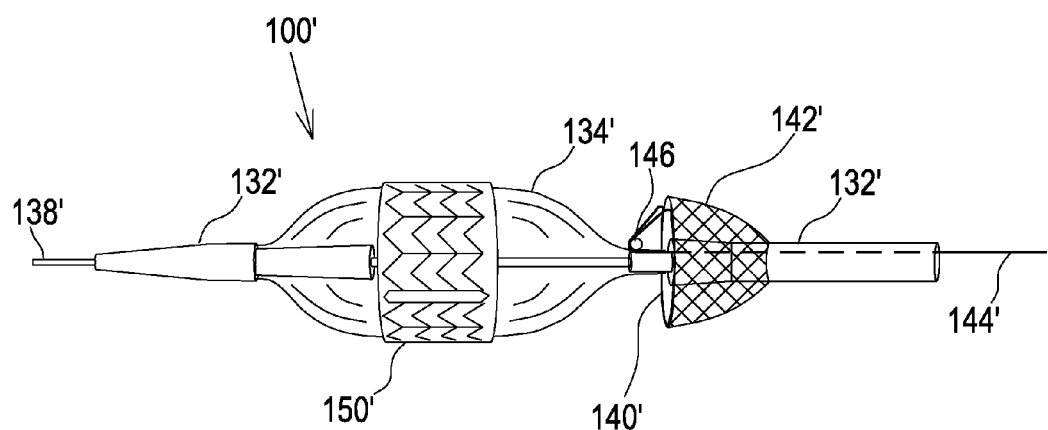
FIG. 30 shows the TAVI of FIG. 29 with the distal embolization device in the open configuration.
Figure 31:
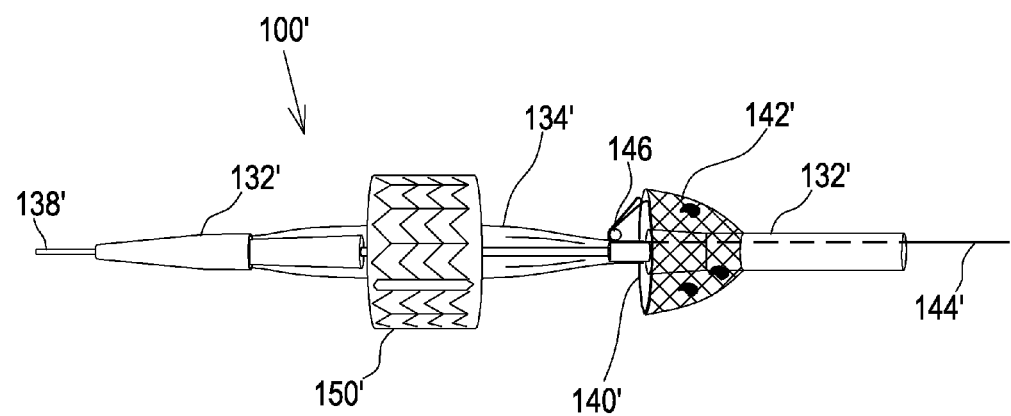
FIG. 31 shows the TAVI of FIG. 30 with the balloon deflated and emboli trapped in the filter of the distal embolization device.

Referring now to FIGS. 30-31 there is shown the mode of action of device 100' which is similar to that of device 100.

In FIG. 30, device 100' is advanced to the native aortic valve annulus, there filter 142' is deployed by the release of retraction filament 144', then balloon 134' is inflated to deploy valve-carrying stent 150'.

As shown in FIG. 31, balloon 134' is then deflated, releasing emboli trapped by filter 142', and filter 142' is then closed by pulling filament 144' and device 100' is then withdrawn from the heart, leaving behind valve carrying stent 150' at the deployment site.

The inventive distal embolization protection component, according to the preferred embodiments of the present invention, can be used for any stent over balloon deployment system, or self-expandable stent, known in the art, as well as any endoluminal method that involves balloon inflation inside any blood vessel like coronary, intra-cerebral arteries, carotid, renal and alike.

Although particular embodiments of the invention have been described and illustrated herein, it is recognized that modifications and variations may readily occur to those skilled in the art and consequently, it is intended that the claims be interpreted to cover such modifications and equivalents.

I claim:

1. An endoluminal catheterization device for providing protection against distal embolization of atherosclerotic debris and thrombi emboli resulting from an endoluminal catheterization procedure, said device comprising:
   an endoluminal dilatation component mounted on a shaft, said shaft having at least one lumen;
   a flexible filter comprising shape memory metal defining a collapsed and deployed shape, wherein said flexible filter is integrally mounted on said shaft; and
   a thin retraction filament extending through said at least one lumen in said shaft and emerging from an opening in said shaft, said retraction filament being attached to said flexible filter for controlling deployment and collapsing of said filter,
   wherein when said retraction filament is released, said flexible filter returns passively to said deployed shape after having been collapsed, and
   wherein said flexible filter, when deployed, traps said atherosclerotic debris and thrombi emboli thus allowing blood flow to continue without interference during said endoluminal catheterization procedure,
   said device further comprising a safety stopper for ensuring that said deployment of said filter occurs before said balloon inflation, wherein said safety stopper is attached to said retraction filament and is situated at the connection point of said inflation tube with said shaft, thus blocking the entrance of inflation fluid for inflating said balloon, when said retraction filament is pulled and said filter is not yet deployed.

2. The device of claim 1, wherein said dilatation component comprises a self expandable stent.

3. The device of claim 1, wherein said dilatation component comprises an angioplasty balloon.

4. The device of claim 3 wherein said angioplasty balloon is surrounded by one of an aortic, pulmonic and tri-cuspid valve-carrying stent, and wherein said angioplasty balloon is capable of being inflated to enable deployment of said valve-carrying stent.

5. The device of claim 4 wherein said valve-carrying stent surrounds said balloon at its center.

6. The device of claim 4 wherein said flexible filter is mounted on said shaft proximal to said dilatation component.

7. The device of claim 6, wherein said thin retraction filament emerges from an opening in said shaft proximal to said dilatation component.

8. The device of claim 7 wherein said valve carrying stent is capable of being advanced retrogradlly to the native valve annulus, for enabling a valve replacement procedure.

9. The device of claim 7 wherein said device comprises one of a stationary and pivotable retraction filament reversing point, said reversing point being situated distally to said filter and proximally to said dilatation balloon, for reversing the direction of said retraction filament back to said filter to enable control of its deployment and collapse.

10. The device of claim 4 wherein said filter is deployed prior to said inflation of said balloon, for enabling capture of said atherosclerotic debris and thrombi emboli as soon as said valve carrying stent is deployed.

11. The device of claim 1, wherein said flexible filter before deployment is approximately 5 to 8 millimeter in diameter, and the maximal size of said filter when it is deployed is 25 to 35 millimeters in diameter.

12. The device of claim 4 wherein said flexible filter is mounted on said shaft distal to said dilatation component.

13. The device of claim 12, wherein said thin retraction filament emerges from an opening in said shaft distal to said dilatation component.

14. The device of claim 12 wherein said valve-carrying stent is capable of being advanced anterogradlly to the native valve annulus, for enabling a valve replacement procedure.

15. The device of claim 1 wherein said flexible filter comprises a filter deployment ring encircling a proximal end of said flexible filter for the purpose of controlling deployment and collapsing of said filter, said filter deployment ring comprising a shape memory metal.

16. A method for performing an endoluminal catheterization procedure and providing protection against distal embolization of atherosclerotic debris and thrombi emboli resulting from said endoluminal catheterization procedure, said method comprising:

inserting an endoluminal catheterization device, comprising an endoluminal dilatation component mounted on a shaft, said shaft having a flexible filter comprising one of a shape memory metal and a thin polymer defining a collapsed and deployed shape, wherein said flexible filter is mounted integrally on said shaft, and a thin retraction filament extends through said shaft and emerges from an opening in said shaft, said retraction filament being attached to said flexible filter, releasing said retraction filament, wherein said flexible filter returns passively to said deployed shape after having been collapsed forcibly by pulling said retraction filament, expanding said dilatation component, wherein said deployed flexible filter, traps atherosclerotic debris and thrombi emboli thus allowing blood flow to continue without interference during said endoluminal catheterization procedure and ensuring that said deployment of said filter occurs before said balloon inflation by providing a safety stopper, wherein said safety stopper is attached to said retraction filament and is situated at the connection point of said inflation tube with said shaft, thus blocking the entrance of inflation fluid for inflating said balloon, when said retraction filament is pulled and said filter is not yet deployed.

17. The method of claim 16, wherein said releasing of said retraction filament is achieved by unlocking a locking device which locks said thin retraction filament onto a filament tube through which said retraction filament passes, wherein said retraction filament is attached to said filter, and thus by releasing said retraction filament said filter is also released and allowed to expand by memory.

18. The method of claim 16, wherein said controlling of said deployment and collapse of said flexible filter comprises a filter deployment ring encircling a proximal end of said flexible filter, said filter deployment ring comprising a shape memory metal.

19. The method of claim 16 wherein said dilatation component comprises an angioplasty balloon surrounded by a valve-carrying stent.

20. The method of claim 19 wherein said endoluminal catheterization procedure is advanced retrogradlly, and said thin retraction filament is being emerged from an opening in said shaft proximal to said dilatation component.

21. The method of claim 20 wherein said shaft comprises a retraction filament reversing point, said reversing point being situated proximally to said dilatation balloon, for reversing the direction of said retraction filament back to said filter to enable control of its deployment and collapse.

22. The method of claim 19 wherein said endoluminal catheterization procedure is advanced anterogradlly and said thin retraction filament is being emerged from an opening in said shaft distal to said dilatation component.

23. An endoluminal catheterization device for providing protection against distal embolization of atherosclerotic debris and thrombi emboli resulting from an endoluminal catheterization procedure, said device comprising:

an endoluminal dilatation component mounted on a shaft, said shaft having at least one lumen, wherein said dilatation component is surrounded by one of an aortic, pulmonic and tri-cuspid valve-carrying stent;

a flexible filter wherein said flexible filter is integrally mounted on said shaft;

a thin retraction filament extending through said at least one lumen in said shaft and emerging from an opening in said shaft, said retraction filament being attached to said flexible filter for controlling deployment and collapsing of said filter;

a stationary and pivotable retraction filament reversing point, said reversing point being situated distally to said filter and proximally to said dilatation component, for reversing the direction of said retraction filament back to said filter to enable control of its deployment and collapse; and wherein said flexible filter, when deployed, traps said atherosclerotic debris and thrombi emboli thus allowing blood flow to continue without interference during said endoluminal catheterization procedure.

* * * * *